(12) United States Patent
Champagne et al.

(10) Patent No.: US 9,974,611 B2
(45) Date of Patent: May 22, 2018

(54) ERGONOMIC SURGICAL GLOVE

(71) Applicant: Exsomed Holding Company LLC, Scottsdale, AZ (US)

(72) Inventors: Lloyd P. Champagne, Phoenix, AZ (US); Jozef Zoldos, Phoenix, AZ (US); Yani Deros, Phoenix, AZ (US)

(73) Assignee: EXOMED INTERNATIONAL IP, LLC, Avarua, Rarotonga (CK)

( * ) Notice: Subject to any disclaimer, the term of this patent is extended or adjusted under 35 U.S.C. 154(b) by 560 days.

(21) Appl. No.: 14/099,803

(22) Filed: Dec. 6, 2013

(65) Prior Publication Data

US 2014/0166521 A1      Jun. 19, 2014

Related U.S. Application Data

(60) Provisional application No. 61/734,027, filed on Dec. 6, 2012, provisional application No. 61/758,728, filed on Jan. 30, 2013, provisional application No. 61/772,463, filed on Mar. 4, 2013.

(51) Int. Cl.
| | | |
|---|---|---|
| *A61B 42/00* | (2016.01) | |
| *A61B 19/04* | (2006.01) | |
| *A61B 42/40* | (2016.01) | |

(52) U.S. Cl.
CPC ............ *A61B 19/045* (2013.01); *A61B 42/00* (2016.02); *A61B 42/40* (2016.02)

(58) Field of Classification Search
CPC ....... A61B 19/04; A61B 19/045; A61B 42/00; A61B 42/40; A61B 42/20; A61B 2017/00424; A41D 19/0055; A41D 19/0062; A41D 19/0079; A41D 19/02

USPC ................................................ 2/161.7, 161.8
See application file for complete search history.

(56) References Cited

U.S. PATENT DOCUMENTS

| | | |
|---|---|---|
| 467,974 A | 2/1892 | Healey |
| 1,279,855 A | 9/1918 | Garvey |
| D61,479 S | 9/1922 | Rice |
| 1,538,262 A | 5/1925 | Ackerman |
| 1,894,066 A | 1/1933 | Smith |
| 2,036,413 A | 4/1936 | Wendell |
| D100,816 S | 8/1936 | Fuchs |
| 2,075,550 A | 3/1937 | Smith |
| 2,173,734 A | 9/1939 | Sidnell |
| 2,335,871 A | 1/1942 | Milligan |
| D133,927 S | 9/1942 | Balzano |
| 2,434,035 A | 1/1948 | De Laney |
| D164,429 S | 9/1951 | Kress |

(Continued)

FOREIGN PATENT DOCUMENTS

| | | |
|---|---|---|
| DE | 654995 C | 1/1938 |
| EP | 2828409 | 9/2015 |

(Continued)

OTHER PUBLICATIONS

USPTO; Notice of Allowance dated Dec. 10, 2015 is U.S. Appl. No. 29/475,635.

(Continued)

*Primary Examiner* — Alissa L Hoey
(74) *Attorney, Agent, or Firm* — Hudak, Shunk & Farine, Co. LPA

(57) ABSTRACT

Disclosed is a surgical glove that alleviates the biasing force associated with bending or abducting the hand and fingers when wearing a surgical glove.

1 Claim, 15 Drawing Sheets

(56) References Cited

U.S. PATENT DOCUMENTS

| | | | |
|---|---|---|---|
| D179,250 S | 11/1956 | Higier | |
| 2,838,759 A | 6/1958 | William | |
| 3,283,338 A * | 11/1966 | Landau | A41D 19/0062 2/161.6 |
| 3,601,816 A * | 8/1971 | Pordes | A41D 19/0062 2/167 |
| 3,728,739 A | 4/1973 | Semp | |
| 3,748,792 A | 7/1973 | Lamb | |
| 3,789,555 A | 2/1974 | Means | |
| 3,867,727 A | 2/1975 | Povlacs | |
| 3,872,514 A | 3/1975 | Liebelt | |
| 3,872,515 A | 3/1975 | Miner | |
| 4,000,524 A * | 1/1977 | Rinehart | A41D 19/02 2/161.6 |
| 4,175,593 A | 11/1979 | Sack | |
| 4,218,778 A | 8/1980 | Stansbury | |
| 4,441,213 A | 4/1984 | Trumble et al. | |
| 4,494,249 A | 1/1985 | Hansson | |
| 4,590,626 A | 5/1986 | Chen | |
| 4,594,736 A | 6/1986 | Connelly | |
| 4,663,783 A | 5/1987 | Obayashi | |
| 4,845,780 A | 7/1989 | Reimers | |
| 4,924,530 A | 5/1990 | Tagaya | |
| 5,317,759 A | 6/1994 | Pierce | |
| 5,323,490 A | 6/1994 | Yarbrough | |
| 5,345,612 A | 9/1994 | Stein | |
| D359,381 S | 6/1995 | Henriquez | |
| 5,442,816 A | 8/1995 | Seketa | |
| 5,500,957 A | 3/1996 | Stein | |
| 5,527,244 A | 6/1996 | Waller et al. | |
| D372,578 S | 8/1996 | Chapman | |
| 5,636,382 A | 6/1997 | Chopko et al. | |
| 5,644,797 A | 7/1997 | Daneshvar | |
| D391,683 S | 3/1998 | Heringer | |
| 5,728,255 A | 3/1998 | Jurrius | |
| 5,781,931 A | 7/1998 | Lee | |
| 5,817,433 A | 10/1998 | Darras | |
| 5,907,870 A | 6/1999 | Monroe et al. | |
| 5,946,720 A | 9/1999 | Sauriol | |
| 5,965,276 A | 10/1999 | Shlenker et al. | |
| 6,081,928 A | 7/2000 | Boume | |
| 6,272,687 B1 | 8/2001 | Cunningham | |
| 6,575,822 B2 | 6/2003 | Lowe | |
| 6,578,205 B1 | 6/2003 | King | |
| D479,972 S | 9/2003 | Cueto | |
| 6,732,378 B2 | 5/2004 | Novak | |
| 6,760,923 B1 * | 7/2004 | Tate | A61B 42/00 2/159 |
| 6,779,199 B1 | 8/2004 | O'Dea | |
| D512,549 S | 12/2005 | Benjamin | |
| D552,827 S | 10/2007 | Muse | |
| RE40,142 E | 3/2008 | Fous | |
| D567,476 S | 4/2008 | Harland | |
| D605,377 S | 12/2009 | House | |
| 7,694,352 B2 | 4/2010 | Kogawa et al. | |
| 7,802,316 B2 | 9/2010 | Hofmann | |
| D628,767 S | 12/2010 | Bengyak | |
| 8,336,119 B2 | 12/2012 | Phelps | |
| D677,030 S | 2/2013 | Wessels | |
| 8,400,256 B2 | 3/2013 | Matthews | |
| D680,695 S | 4/2013 | Lin et al. | |
| 8,453,266 B2 | 6/2013 | Bevier et al. | |
| 8,505,115 B2 | 8/2013 | Matsuoka | |
| 8,512,615 B1 | 8/2013 | Amdur et al. | |
| 8,572,765 B2 | 11/2013 | Tao | |
| D707,526 S | 6/2014 | Daniel | |
| D733,972 S | 7/2015 | Szalkowski et al. | |
| D735,968 S | 8/2015 | Furlong | |
| D739,993 S | 10/2015 | Mathota | |
| 9,179,718 B2 * | 11/2015 | Anstey | A41D 19/015 |
| D754,929 S | 4/2016 | Champagne | |
| 9,370,209 B2 | 6/2016 | Hull | |
| D747,070 S | 10/2016 | Kelly | |
| 9,622,523 B2 | 4/2017 | Champagne | |
| 2002/0166156 A1 | 11/2002 | Clark et al. | |
| 2004/0255362 A1 | 12/2004 | Soerens | |
| 2005/0015846 A1 | 1/2005 | Vistins et al. | |
| 2006/0005295 A1 | 1/2006 | Mattesky | |
| 2006/0191056 A1 | 8/2006 | Bottcher | |
| 2006/0218697 A1 | 10/2006 | Modha | |
| 2007/0074331 A1 | 4/2007 | Bitzer | |
| 2008/0000010 A1 | 1/2008 | Erickson et al. | |
| 2008/0134411 A1 | 6/2008 | Shapiro | |
| 2008/0155726 A1 | 7/2008 | Anclien | |
| 2008/0244808 A1 * | 10/2008 | Chaen | A41D 19/02 2/161.2 |
| 2010/0050311 A1 | 3/2010 | Tsai | |
| 2011/0258751 A1 * | 10/2011 | Matsuoka | A41D 19/02 2/159 |
| 2011/0277215 A1 | 11/2011 | Lee et al. | |
| 2011/0296582 A1 | 12/2011 | Bevier et al. | |
| 2012/0042437 A1 | 2/2012 | Matthews | |
| 2012/0047616 A1 | 3/2012 | Wood | |
| 2013/0061369 A1 | 3/2013 | Lim | |
| 2013/0263355 A1 * | 10/2013 | Mavraganes | A41D 19/0027 2/161.7 |
| 2013/0291282 A1 | 11/2013 | Anstey | |
| 2014/0020152 A1 | 1/2014 | Yang | |
| 2014/0150162 A1 | 6/2014 | Guan | |
| 2014/0208480 A1 | 7/2014 | Champagne et al. | |
| 2014/0208481 A1 | 7/2014 | Champagne | |
| 2014/0259283 A1 * | 9/2014 | Govindasamy | A61B 19/04 2/161.7 |
| 2015/0189932 A1 | 7/2015 | Champagne et al. | |
| 2016/0081408 A1 | 3/2016 | Hull | |
| 2016/0174634 A1 * | 6/2016 | Schatzberg | B29C 41/14 2/163 |

FOREIGN PATENT DOCUMENTS

| | | |
|---|---|---|
| EP | 2950739 | 11/2015 |
| FR | 476889 A | 9/1915 |
| FR | 1141139 A | 8/1957 |
| GB | 2 148 094 A | 5/1985 |
| WO | 199639055 A1 | 12/1996 |
| WO | 2013126727 A1 | 8/2013 |

OTHER PUBLICATIONS

USPTO; Office Action dated May 18, 2016 in U.S. Appl. No. 14/542,217.

USPTO; Restriction Requirement dated Jun. 17, 2016 in U.S. Appl. No. 14/133,424.

USPTO; Non-Final Office Action dated Oct. 21, 2016 in U.S. Appl. No. 14/133,438.

USPTO; Non-Final Office Action dated Jun. 17, 2015 in U.S. Appl. No. 14/542,217.

USPTO; Final Office Action dated Dec. 23, 2015 in U.S. Appl. No. 14/542,217.

USPTO; Office Action dated Nov. 2, 2016 in U.S. Appl. No. 14/133,424.

USPTO; Office Action dated Jun. 17, 2015 in U.S. Appl. No. 14/542,217.

PCT; International Search Report and Written Opinion dated Feb. 25, 2014 in Application No. PCT/US2013/073727.

PCT; International Search Report and Written Opinion dated Apr. 17, 2014 in Application No. PCT/US2014/013940.

USPTO; Notice of Allowance dated Oct. 24, 2016 in U.S. Appl. No. 29/557,960.

USPTO; Notice of Allowance dated on Dec. 19, 2016 in U.S. Appl. No. 14/542,217.

USPTO; Final Office Action dated Mar. 21, 2017 in U.S. Appl. No. 14/133,438.

USPTO; Final Office Action dated Mar. 24, 2017 in U.S. Appl. No. 14/133,424.

USPTO; Advisory Action dated Apr. 12, 2017 in U.S. Appl. No. 14/133,424.

(56) References Cited

OTHER PUBLICATIONS

USPTO; Advisory Action dated Apr. 25, 2017 in U.S. Appl. No. 14/133,438.

* cited by examiner

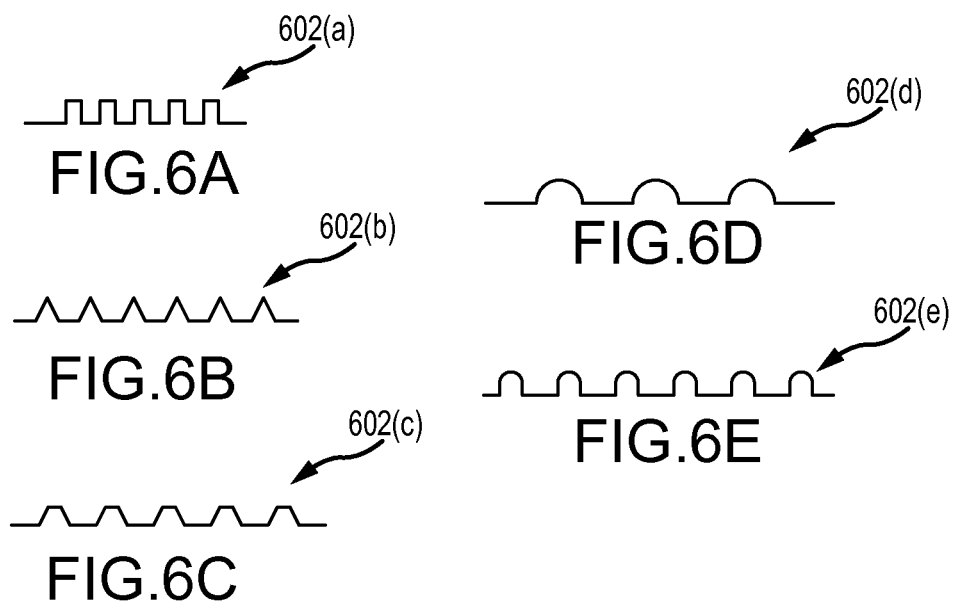
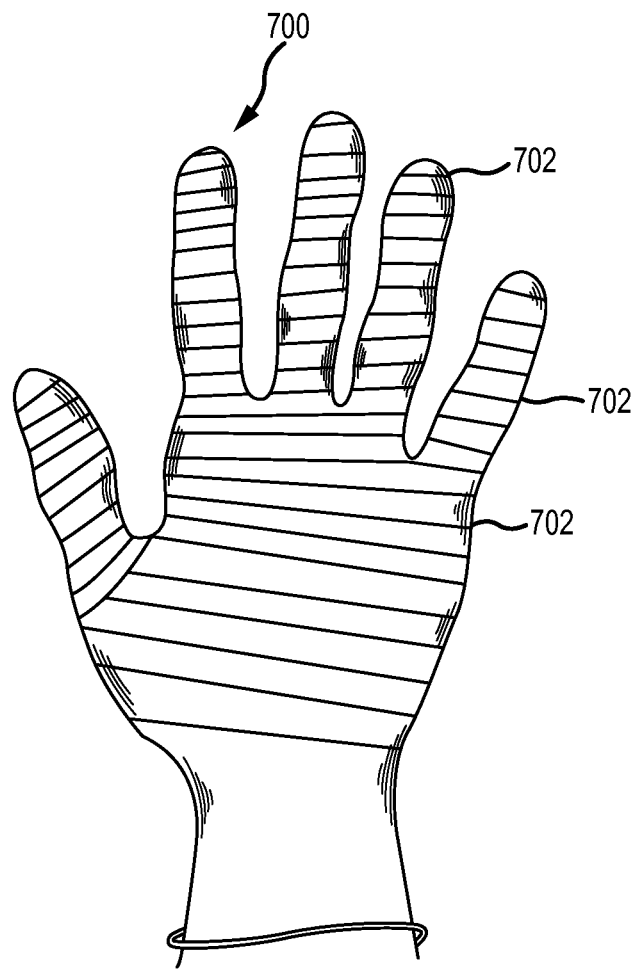

ERGONOMIC SURGICAL GLOVE

FIELD OF THE INVENTION

The present invention relates to a surgical glove formed to be all or partially in essentially the relaxed shape of a human hand, potentially including being formed in a flexed position at one or more of the finger joints, palm and/or dorsum of the hand. The invention also relates to specific features on the glove to alleviate biasing forces related to movement of the hand and to assist the glove in conforming to the movement of the hand.

BACKGROUND OF THE INVENTION

Surgical gloves are known in the art. The gloves are usually manufactured from latex or latex-free substitutes and fit snugly on the hand. Surgical gloves are often initially formed in a shape approximately the same as a hand when pressed flat on a surface or extended to be essentially flat or straight, such as shown in FIG. 1 and FIG. 2. In that position, the fingers extend outward, essentially straight from the palm (in this context "straight" means there is essentially no bend at any of the joints). In this position, the thumb is oriented in a flat plane or is slightly abducted away from the palm. A problem with the standard glove shape is that the relaxed hand is not naturally in a flat position with the fingers essentially straight. As shown in FIGS. 3-4, when in its normal, relaxed position, which is also called the normal hand cascade position, the joints of the fingers (the fingers and thumb also collectively referred to herein as "digits") are naturally in a flexed position, with the thumb in a different plane than the fingers. This normal position does not match the shape of a standard surgical glove.

If a medical professional wears surgical gloves for a long period, such as when he/she is performing a long procedure or is performing multiple successive procedures in a given period of time, the professional's fingers and hands can become tired or fatigued because of constantly overcoming the biasing forces of the surgical glove(s) in order to flex the fingers and hand (either to a closed position, open position, or both).

Consequently, when a standard surgical glove is placed on a hand, the material of the glove biases the fingers away from the normal, relaxed position to the less natural straight position. When a medical professional then uses his/her hand during a medical procedure, in order to flex the fingers, the biasing force of the glove material must be overcome. For example, FIG. 5 shows a hand 500 of a medical professional grasping a dental instrument 502. Fingers 504-510 are flexed to grasp the instrument 502, and to do so, the biasing force of surgical glove 512 must be overcome. This biasing force is even greater if two gloves are placed on the hand, which is frequently done to increase protection for the medical professional in the event that the outer glove tears or is punctured or if there is a random manufacturing defect resulting in a perforation.

In addition to standard surgical gloves being formed in a straight position, they have no structure to permit the expansion or contraction of the dimensions of portions of the hand. For example, the circumference of a flexed finger (such as when the fingers are flexed towards the palm of the hand) is greater than its circumference when relaxed or in the straight position. This concept is illustrated in FIG. 22, showing a 20% increase in circumference in a female index finger and a 22% increase in circumference in a male index finger. If gloves are designed so they tightly fit fingers that are in the straight position, and then the fingers are flexed, the fingers must also overcome the biasing force of the glove material that restricts digital expansion. Consequently, there is a need for extra material during flexion of the fingers so the portion of the glove covering the portion of the finger (referred to herein as the "finger portions") that expands can (1) permit expansion when the finger is flexed, and (2) contract back into shape and is not used when the finger is not flexed. The biasing force of gloves also includes adduction of the fingers, a force tending to keep the fingers together in line rather than in their natural cascading position. This is another biasing force that must be overcome when using standard surgical gloves.

Glove designs with baggy, or loose-fitting portions, at one or more areas are known, but such gloves are not optimal for a medical professional performing procedures that require fine, precise work. Glove designs are also known that have ribs at some areas, but while the ribs may help to some degree, they do not overcome the problems described herein.

It would be beneficial for medical professionals to have surgical gloves that minimize biasing forces, that include a minimal amount of excess, loose or baggy material, and that are relatively simple to manufacture, so they are cost effective.

SUMMARY OF THE INVENTION

Aspects of the present invention are surgical gloves (also referred to herein as "gloves") that utilize shapes with the finger portions positioned more towards the natural, relaxed position of fingers. Preferably, the gloves reduce the biasing force inherent in standard gloves when (1) closing the hand, (2) opening the hand, and (3) closing and/or opening the fingers and/or moving the thumb. As set forth in more detail below, a glove according to the invention may also be combined with, or instead include: (a) special relaxing or distressing features (also referred to as "patterns") at one or more positions, (b) thinner portions of material at one or more positions, and/or (c) different materials with different flexibility characteristics at one or more positions.

Exemplary surgical gloves are essentially formed either partially or entirely in the approximate shape of a relaxed hand, examples of which are shown in FIGS. 3 and 4. Because of the glove's shape, the amount of biasing force that must be overcome to flex the fingers, move the thumb, close the hand, and/or move the thumb to a position where it is pressed against one of the fingers is reduced. Medical professionals can therefore utilize the gloves for longer periods without their fingers or hands becoming as tired or fatigued as when using conventional surgical gloves.

A surgical glove according to various embodiments of the invention is formed with pre-formed angles (also referred to herein as "flex angles") at one or more of the metacarpophalangeal (MCP) joints, proximal interphalangeal (PIP) joints and distal interphalangeal (DIP) joints in the finger portions. Examples of flex angles are shown in FIGS. 3-4. The "flex angle" for each digit is the angle formed in the medial plane of the finger portion measured at the respective joint at the dorsal exterior surface of the glove as shown for the hand in FIG. 21. In one example, one or more of the portions of the glove corresponding to the MCP joints may be formed at a flex angle, and/or one or more of the portions of the glove corresponding to the PIP joints may be formed at a flex angle, and/or one or more of the portions of the glove corresponding to the DIP joints may be formed at a flex angle. Any combination or permutation of glove portions corresponding to any combination of joints on any combination of fingers and/or the thumb and/or the palm can include a flex angle as described herein.

In accordance with further examples, MCP joint portions of a glove have a greater flex angle than the PIP and DIP positions to render a glove that more closely replicates the natural, cascading position of the fingers and permits the hand to be in an open, usable position.

Additionally, the portion of the glove that retains the thumb (referred to herein as the "thumb portion") may have portions at the thumb MCP and IP joints that are formed at respective flex angles, corresponding to essentially the angle of the relaxed position of the thumb. Further, the overall position of the thumb portion of the glove may be essentially in the thumb's natural, relaxed position, e.g., that of abduction from the palm with some flexion at the MCP and IP joints.

Exemplary gloves can include a texturing or patterning, or other design features, such as patterns, ripples, ribs, textures or bumps, or a combination thereof (collectively, "pattern" or "patterns") formed as part of the glove; such pattern making the glove easier to flex. The patterns provide extra material, which is used when a hand or digit flexes in a certain manner. These patterns can be formed on the outer or inner surface of the glove, and are preferably on the outer (or outside) surface.

Patterns can be added to any relevant portion of the glove. As one example, a glove as described herein can include longitudinal ribs along parts of one or more fingers or the thumb to allow for expansion of the digit (i.e., an increase in circumference during flexing). Furthermore, a pattern can exist in one or more spaces between the fingers, thus reducing the biasing force of the glove in this area and allowing easier abduction or movement. Also, if the glove formed in a flexed position, there can be a slight bias toward flexion, rather than extension (the opening of the hand), so features can be added on the palm side of the glove, such as at the finger creases and/or center of the palm to relieve some of the force of extension.

Further, exemplary gloves can include patterns and/or shapes, such as flex angles, that reduce the biasing force to open the hand, such that that a glove is not completely in the relaxed hand position.

In accordance with further exemplary embodiments, a glove may include material of various thicknesses. For example, a glove can include material of a first thickness corresponding to most of the hand, and have material that is thinner when the glove stretches—e.g., near various joints and/or on the dorsum or palm.

In accordance with yet further exemplary embodiments, a glove includes material in some areas that is more flexible in areas where the digits and hand flex, and may include another material that is more puncture resistant than the glove material in other areas. For example, the glove can include reinforced material on the fingertips and/or palm areas.

Gloves in accordance with the present disclosure can include any combination of materials, flex angles, and features as described herein.

As set forth in more detail below, various gloves as described herein can accommodate the movement of the hand and digits with reduced biasing force, and at the same time fit properly (and preferably not be oversized or baggy) throughout the hand's entire range of motion, especially the range used during a medical procedure.

BRIEF DESCRIPTION OF THE DRAWINGS

FIG. 6A is a close-up, side illustration of an exemplary pattern suitable for the material of the glove of FIG. 6.

FIG. 6B is a close-up, side illustration of another exemplary pattern suitable for the material of the glove of FIG. 6.

FIG. 6C is a close-up, side illustration of another exemplary pattern suitable for the material of the glove of FIG. 6.

FIG. 6D is a close-up, side illustration of another exemplary pattern suitable for the material of the glove of FIG. 6.

FIG. 6E is a close-up, side illustration of another pattern suitable for the material of the glove of FIG. 6.

FIG. 7 depicts a top view (wherein the flex angles of the joints cannot be readily seen) of an exemplary glove that includes a pattern of ribs.

DETAILED DESCRIPTION OF PREFERRED EMBODIMENTS

Figure 1:
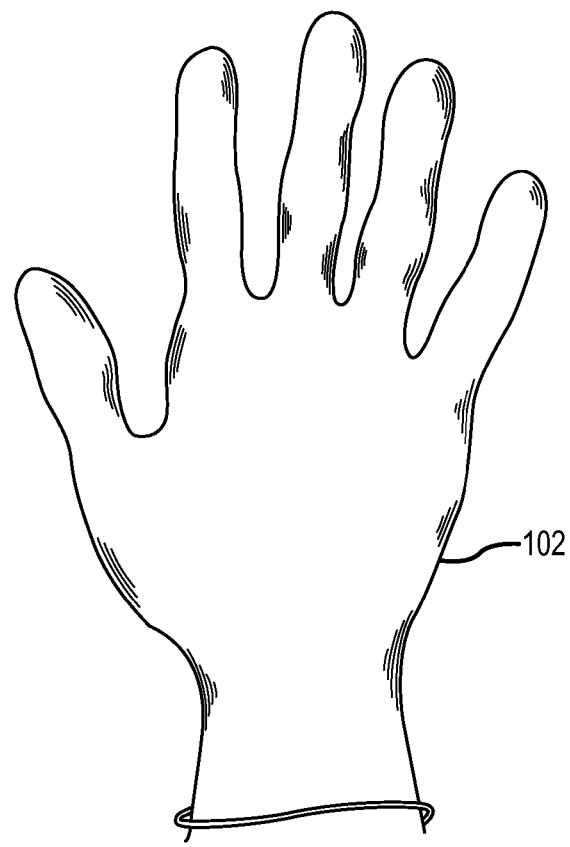
FIG. 1 depicts a hand that is flat with the fingers extending outward from the palm in essentially a straight position, with a surgical glove on the hand.
Figure 2:
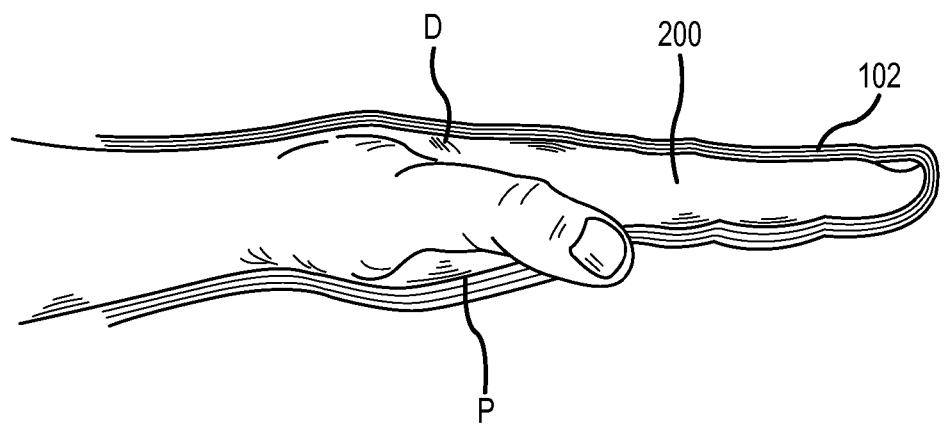
FIG. 2 depicts a partial cross-sectional view of the surgical glove of FIG. 1.
Figure 3:
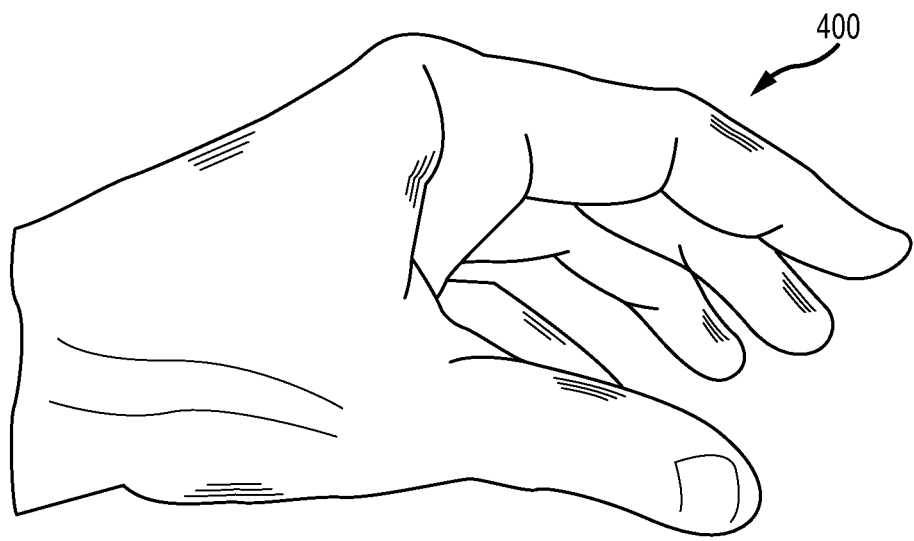
FIG. 3 depicts a hand in a suspended, normal relaxed position and not resting on a surface.
Figure 12:
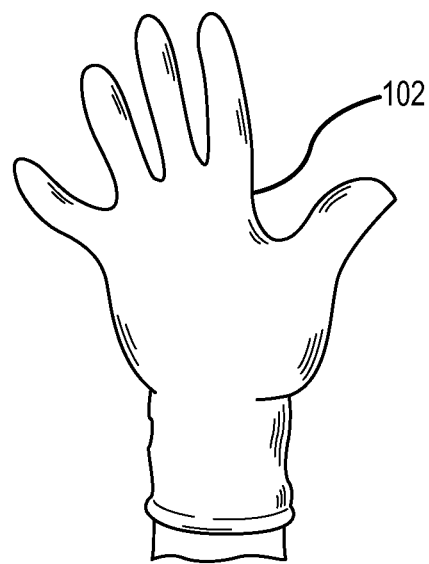
FIG. 12 illustrates a hand with a standard surgical glove wherein the hand is biased to flexion.
Figure 13A:
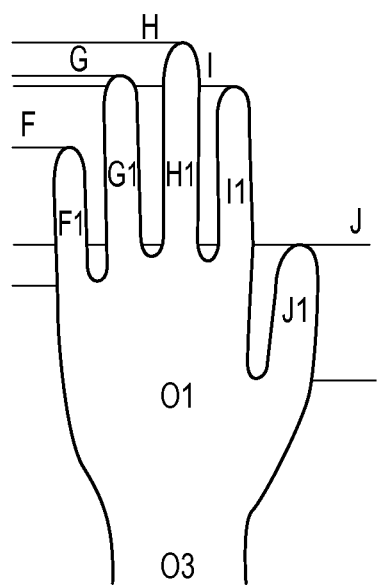
FIG. 13A illustrates a palm view of a standard surgical glove.
Figure 13B:
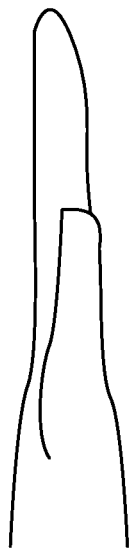
FIG. 13B illustrates a side view of the glove of FIG. 13A.

Turning now to the drawings where the purpose is to describe exemplary embodiments of the invention and not to limit the same, FIG. 1 illustrates a top view, FIG. 2 illustrates a side view, and FIG. 12 illustrates a bottom or palm view of a hand 200 in a relatively flat position with a surgical glove 102 thereon. A shape of a conventional glove is further illustrated in FIGS. 13(a) and 13(b), which illustrate a palm view and a side view of the conventional glove.

Figure 17:
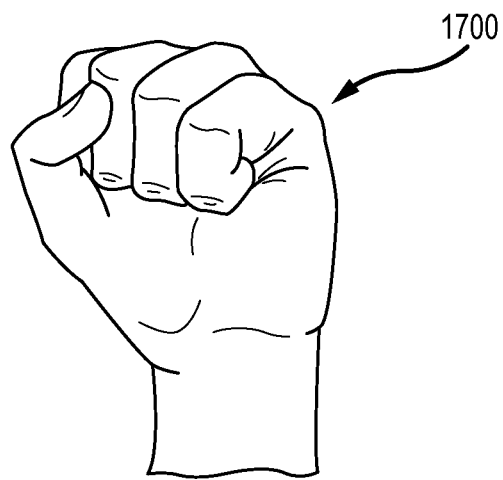
FIG. 17 illustrates a hand without a surgical glove, wherein the hand is fully biased to the flexion position.
Figure 18A:
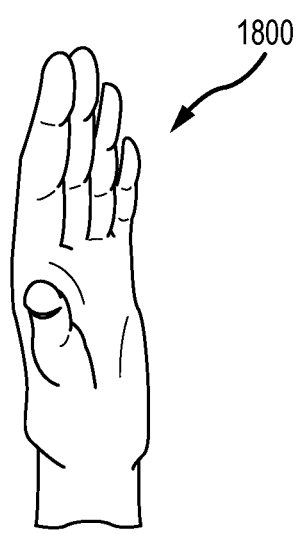
FIG. 18A illustrates a side view of a hand in the straight position, which is the position in which most current surgical gloves are formed.
Figure 18B:
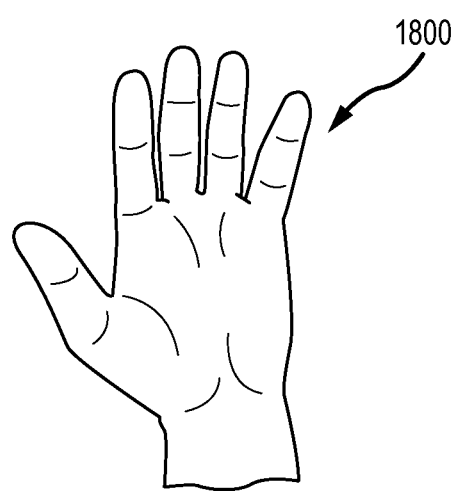
FIG. 18B illustrates a palm view of the hand of FIG. 18A.
Figure 19A:
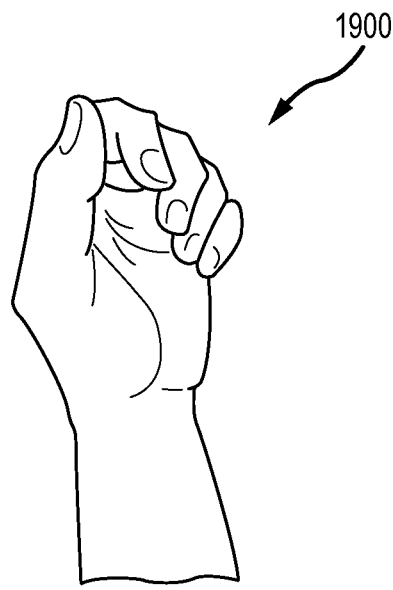
FIG. 19A illustrates a side, perspective view of a hand in a fully relaxed position.
Figure 19B:
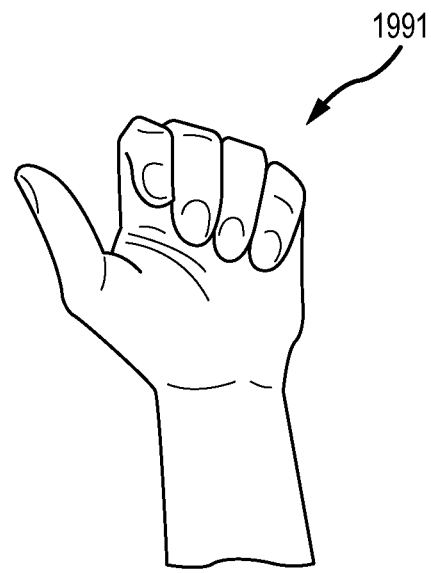
FIG. 19B illustrates a front view of the hand in FIG. 19A.
Figure 20:
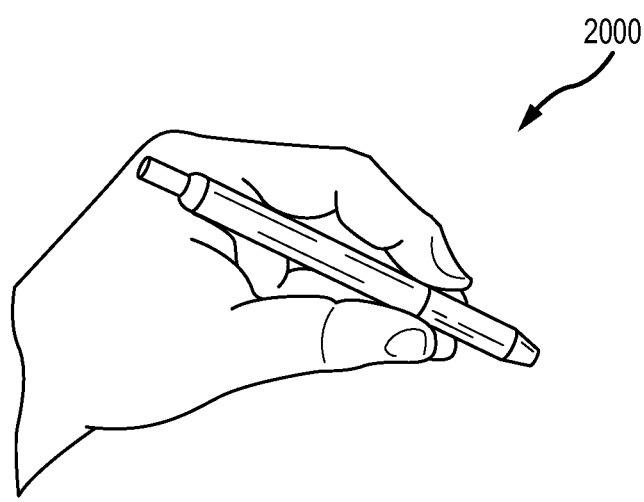
FIG. 20 illustrates a hand in a working position.

To facilitate understanding of the gloves described herein, various hand positions are illustrated in FIGS. 17-21. FIG. 17 illustrates a hand 1700 biased to flexion. FIG. 18A illustrates a side view of a hand 1800 in the straight position, which is the position in which standard surgical gloves are formed. FIG. 18B illustrates a palm view of hand 1800. FIG. 19A illustrates a side, perspective view of a hand 1900 in a fully relaxed position and having cascading fingers. FIG. 19B illustrates a front view of the hand 1900. FIG. 20 illustrates a hand 2000 in a working position.

As is known, an MCP joint is a metacarpophalangeal joint. A PIP joint is a proximal interphalangeal joint. A DIP joint is a distal interphalangeal joint. An IP joint is an interphalangeal joint. And, a CMC joint is a carpometacarpal joint.

A thumb generally includes three joints. The most proximal thumb joint is the CMC joint between the trapezium and the thumb metacarpal. The thumb MCP joint is between the metacarpal and the proximal phalanx of the thumb. The distal most thumb joint is the IP or interphalangeal between the proximal and distal phalanges of the thumb.

Each finger portion, including the index, middle, ring and little fingers, has four joints including the CMC, MCP, PIP and DIP joints. The CMC joint of each finger is between the metacarpal and the carpal bone. The MCP joint of each finger is between the metacarpal and the proximal phalanx. The PIP joint of each finger is between the proximal and middle phalanges. The DIP joint of each finger is between the middle and distal phalanges.

Figure 4:
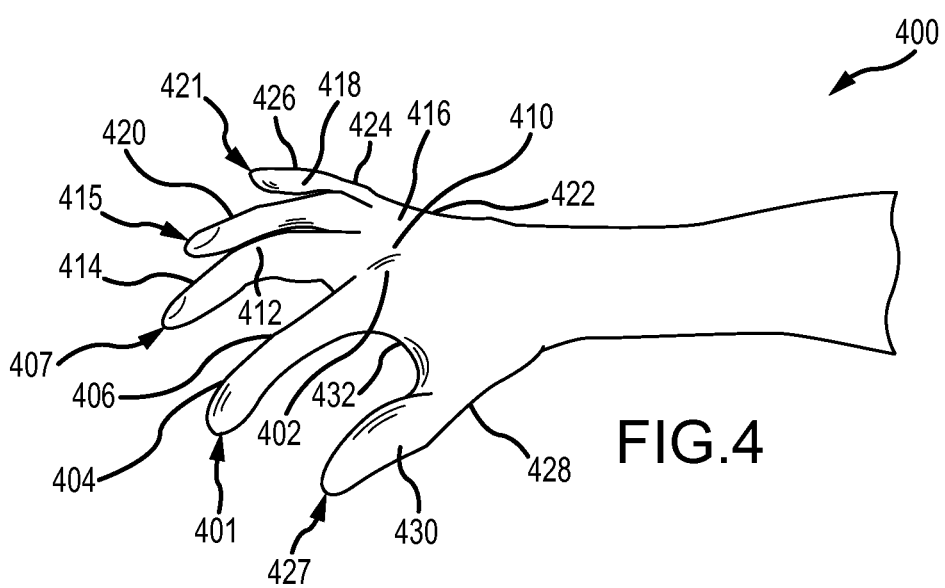
FIG. 4 illustrates a hand in a normal, relaxed position.
Figure 5:
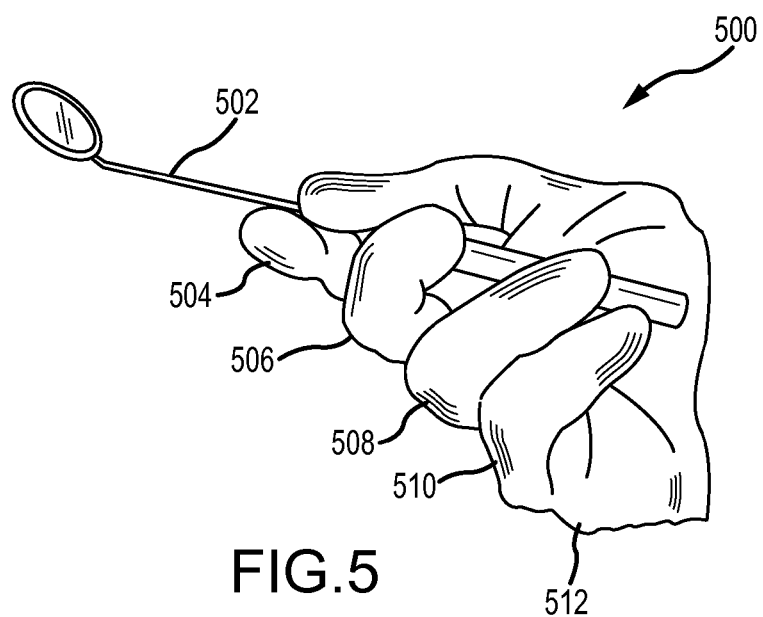
FIG. 5 depicts a hand with a conventional surgical glove thereon, wherein the hand is grasping a dental instrument.

Turning to FIG. 4, respective portions of a hand 400 are shown. Index finger 401 has MCP joint 402, DIP joint 404, and PIP joint 406. Middle finger 407 has MCP joint 410, PIP joint 412, and DIP joint 414. Ring finger 415 has MCP joint 416, PIP joint 418 and DIP joint 420. Little finger 421 has MCP joint 422, PIP joint 424 and DIP joint 426. Thumb 427 has MCP joint 428 and IP joint 430. There is a space 432 between the thumb 427 and index finger 401. Not readily visible are the CMC joints of the fingers and thumb.

Surgical gloves as described herein can be formed (i.e, molded) of any suitable elastomeric material, such as medical-grade natural rubber latex or synthetic rubber material in accordance with ASTM D3577. Exemplary synthetic rubber materials include polychloroprene (neoprene), polyisoprene, styrene butadiene, styrene ethylene butadiene. Other suitable materials include nitrile and vinyl (polyvinylchloride).

Figure 14:
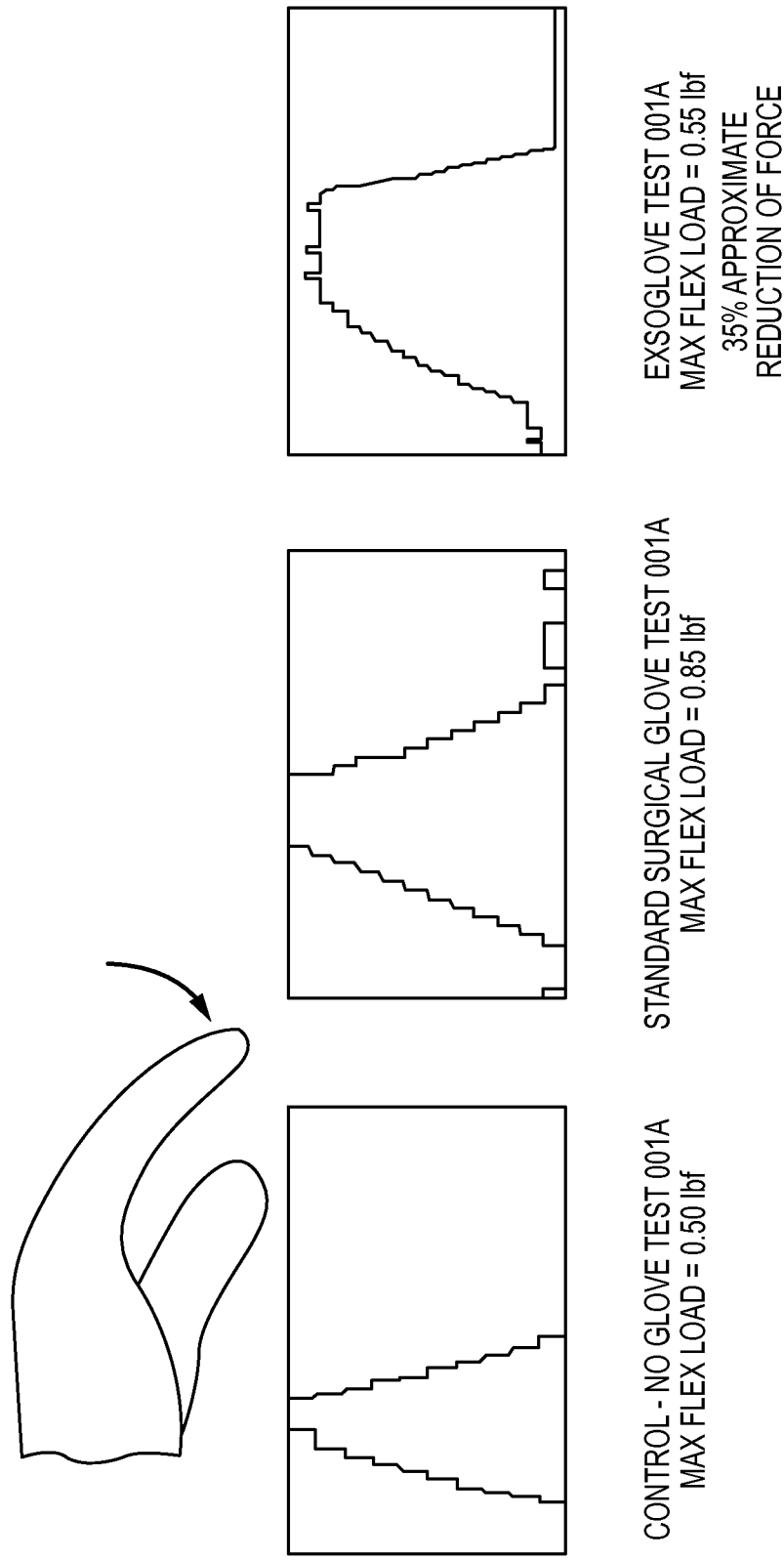
FIG. 14 illustrates comparative strain forces of fingers moving from the straight to the flexed position for various gloves.

Various embodiments of the glove designs described herein can be used alone or in any combination with the other designs and features noted herein. As noted herein, various advantages of the gloves herein described include a reduction of a biasing forces when the hand is opened and/or closed. FIG. 14 illustrates an exemplary reduction in flex load, compared to standard gloves. In this specific illustrated example, gloves in accordance with the present description reduced a flex load by about 35%, although the invention is not limited to this amount.

Flex Angles

Figure 21:
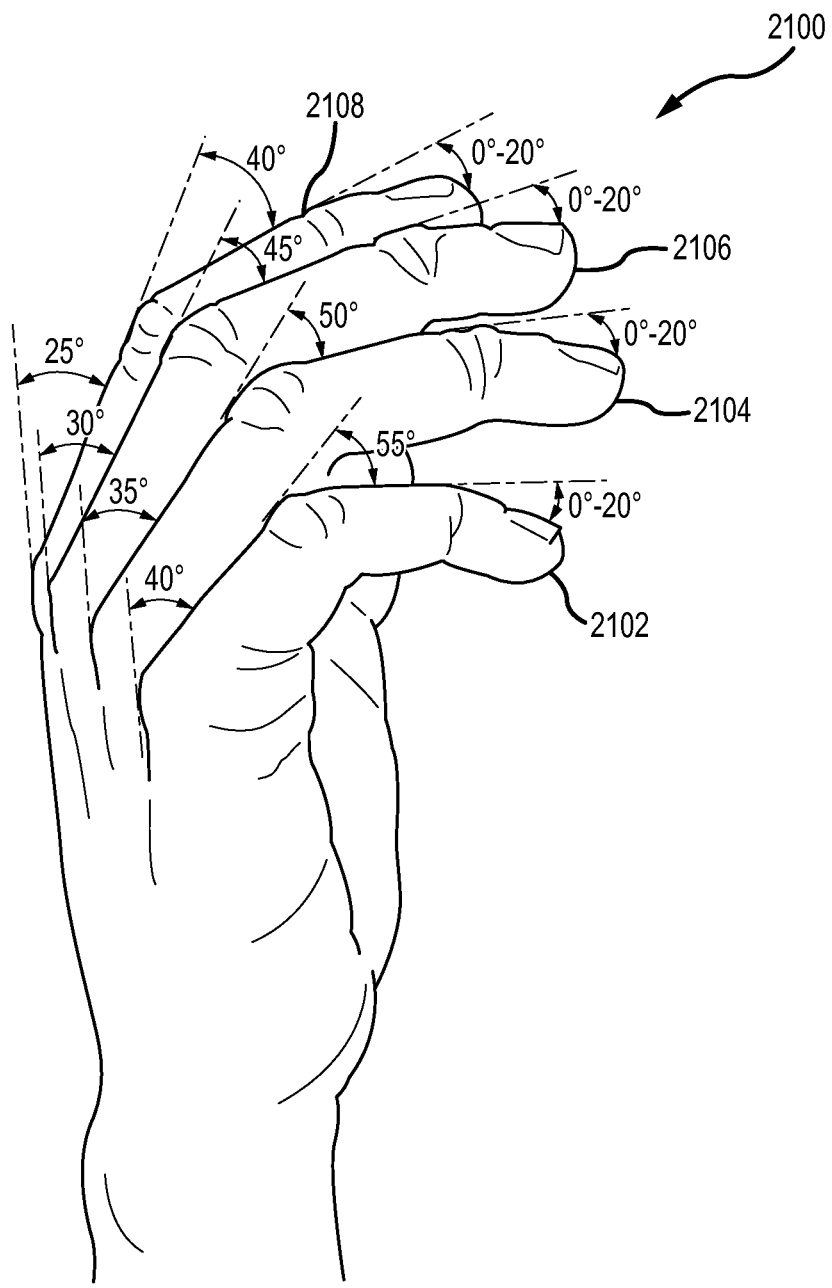
FIG. 21 illustrates a hand in a more natural position, but not the fully relaxed position, and shows the angles of the finger joints when in this position.

Exemplary gloves according to various embodiments of the invention are formed so the portions of the gloves corresponding to the fingers and thumb of a hand are more generally in a normal, relaxed hand position, but not entirely in the relaxed position, such as the position illustrated in FIG. 21. In this manner the hand can be closed and opened with limited resisting biasing forces on one or more of the digits and/or hand caused by the glove. By way of examples, portions of a glove corresponding to one or more of the MCP joints (i.e. an "MCP joint portion"), one or more of the PIP joints (i.e., a "PIP joint portion") and/or one or more of the DIP joints (i.e., "a DIP joint portion") and for the thumb, the IP joint (i.e. the "IP joint portion") of a hand can be formed at a flex angle. A surgical glove according to exemplary embodiments the invention preferably includes one or more of the following portions formed as follows: (a) the portion corresponding to the MCP joint of the index finger is formed at a flex angle of 10-45°, (b) the portion corresponding to the MCP joint of the middle finger is formed at a flex angle of 10-45°, (c) the portion corresponding to the MCP joint of the ring finger is formed at a flex angle of 15-50°, and (d) the portion corresponding to the MCP of the little finger formed at a flex angle of 20-55°.

Further, the following portions of the glove may be formed as follows: (a) the portion corresponding to the PIP joint of the index finger is formed at a 5-45° flexed angle, (b) the portion corresponding to the PIP joint of the middle finger is formed at a 5-50° flexed angle, (c) the portion corresponding to the PIP joint of the ring finger is formed at a 10-55° flexed angle, and (d) the portion corresponding to the PIP joint of the little finger is formed at a 15-60° flexed angle.

Additionally or alternatively, one or more of the following portions of a glove corresponding to the thumb may be formed as follows: (a) the portion corresponding to the MCP joint of the thumb is formed at a flexed angle of 10-45°, and (b) the portion corresponding to the IP joint of the thumb is formed at a flexed angle of 20-50°.

In one embodiment, the portions of the glove corresponding to the MCP joints have greater flex angles than either the PIP and DIP joints, such that the fingers in the hand remain open to some degree, rather than being in their fully relaxed position. One embodiment of preferred flex angles are approximately:

|  | Index finger | Middle finger | Ring finger | Little finger |
| --- | --- | --- | --- | --- |
| MCP joint | 25° | 25° | 30° | 35° |
| PIP joint | 15° | 15° | 20° | 25° |
| DIP joint | 15° | 15° | 20° | 25° |

Although these angles are less than the complete relaxed position of the hand, they allow for: ease of manufacturing, helping to keep the hand open to some degree, and preventing too much bias against opening or closing the hand.

Any of the afore-mentioned joint flex angles could possibly be varied beyond the stated ranges to better approximate the shape of a hand in a position to reduce biasing forces when the hand opens or closes.

Another aspect of the invention is that when in a relaxed position, the finger portions of the glove may be in a cascading position moving from the index finger portion to the little finger portion, with the flex angles of the joints of each finger portion varying. An example of a hand 2100 including cascading fingers 2102-2108 is illustrated in FIG. 21. Some embodiments of the gloves disclosed herein include this cascading feature. More specifically, this means that the gloves include joint portions formed at an angle (i.e. a flex angle) so that the finger portions and thumb portion have a curvature toward the palm region of the glove. One way in which a glove according to the invention compensates for this cascading position is by providing different flex angles, or features to permit flexing, at the various joints. Exemplary angles for the cascading digits for a hand are illustrated in FIG. 21.

Additionally, the palm region of the glove may be formed at a suitable flex angle, such as between 10°-30°. Moreover, a glove according to the invention may have the thumb portion formed in a more natural position with the thumb in a different plane than the fingers.

Patterns

Figure 6:
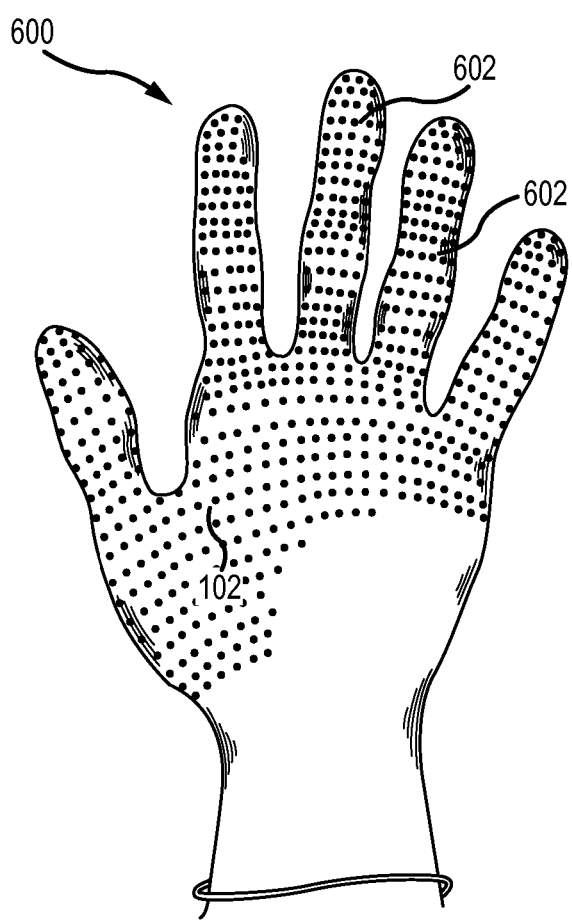
FIG. 6 depicts a top view (wherein the flexed angles of the joints cannot be readily seen) of an exemplary glove that includes a pattern.

A glove according to the exemplary embodiments of the invention can additionally or alternatively have a pattern formed therein at various positions that allows easier flexing of the glove material. Some exemplary patterns are shown in FIGS. 6-6E and each provides additional material for opening and/or closing the hand to reduce biasing forces when stretched, and reduce or eliminate a baggy fit when not stretched. The pattern may be one or more of the following:

(1) Any feature with about 10 mm or less of total height or depth (relative to the outer surface of the glove) that permits a glove to flex with less force when the hand is opened, closed or both.

(2) The material forming the glove may be ribbed, wherein the ribs (which are folds of material) include excess material to permit expansion of the glove and the ribs may extend about ⅛" or less beyond the outer surface of the glove on either the dorsum side, palm side, between the fingers, between the thumb and fingers, or some combination thereof. FIG. 2 illustrates a dorsum D side of hand 200 and a palm side P of hand 200.

(3) The material forming the glove can have a pattern of (e.g., alternating) raised portions and/or depressions, wherein the center of each raised portion or depression is preferably no greater than ¼" inches apart from other portions, and most preferably no greater than ⅛" to ¹⁄₃₂" apart. The raised or depressed portions are preferably formed in one or more of cross-sectional shapes from the group consisting of: semi-oval, semi-circle, square, rectangular, triangular, three-sided pyramidal and four-sided pyramidal. The pattern may follow the natural contour of the hand where desired. This can create nonlinear and asymmetrical patterns.

A glove can include a more concentrated pattern of patterns proximate areas corresponding to areas of the digits and hand that bend or stretch, thereby allowing easier bending at the areas of the glove that need to bend more, such as at one or more of the MCP, PIP, DIP, or IP joint portions, or in area 32 between the thumb portion and index finger portion, or in the web spaces between the other finger portions. As another example, a pattern may be present and/or more concentrated along the axis of the dorsum of the little finger portion, or be more concentrated from the mid hand to the mid proximal phalanx. Or, the pattern may cover any portion of the dorsum region or palm region. On the index finger portion, the pattern may cover the distal hand to the proximal phalanx. The pattern may be biased toward the ulnar side of the hand where biasing forces are greatest. On the thumb MCP joint portion, the pattern may predominate on the dorsum region, but might extend into area 32. Additionally, the pattern may be placed along the longitudinal axis (i.e., where the finger portion or thumb portion have a length and the longitudinal axis for each is an imaginary axis which extends along the length of the finger portion or thumb portion) of one or more of the fingers portion and/or thumb portion.

A glove including a pattern might include the same pattern or different patterns, such as one pattern at one or more of the joints, and another between the spaces between the fingers. For example, alternating raised portions or depressions in the form of a four-sided pyramid may be at any suitable location on the gloves, including on part of or the entire palm side of the glove, and there may be ribs running into the spaces between the fingers, or on the flexor surface of the gloves to relieve biasing forces of extending fingers associated with pre-relaxed surgical gloves. The ribs allow easier expansion to decrease the loads on the digits with abduction of the fingers or wide stretching of the hand, in the same fashion as one would need to play far apart piano keys. The glove can include a pattern over or under any of the joints of one or more of the digits. Further, a pattern can be placed in the mid palm to provide some relaxation during maximal extension of the fingers.

Some non-limiting examples of gloves having different patterns are illustrated in FIGS. 6-11. FIG. 6 illustrates a glove 600 having a pattern 602. As illustrated, pattern 602 covers all of the joints of the digits, the space between the thumb and index finger, and the spaces between each finger. Pattern 602, or any suitable pattern used with the gloves described herein, could cover any suitable portion of the glove, such as one or more of: the portion corresponding to one or more joints, the portion corresponding to the space between the thumb and index finger, any or all spaces between the fingers, the dorsum, and the palm.

FIGS. 6A-6E illustrate close up, side views of exemplary structures suitable for pattern 602. FIG. 6A illustrates pattern 602(*a*) as raised square or rectangular sections. FIG. 6B illustrates pattern 602(*b*) as raised triangular sections, which would be pyramidal if viewed in three dimensions. FIG. 6C illustrates pattern 602(2) as raised flat-topped pyramidal sections. FIG. 6D illustrates pattern 602(*d*) as raised broad partial ovoid or partial spherical sections. FIG. 6E illustrates pattern 602(*e*) as raised dome-like sections. Any suitable structures, or combination of structures, however, could be used to form pattern 602.

FIG. 7 illustrates a glove 700 according to various embodiments of the invention with ribs 702 to assist with easier flexing. Exemplary ribs 702 are formed in the material of glove 700 and are preferably no higher than about 2 mm, although any suitable height can be used. The spacing between the ribs may be any suitable spacing and may vary at different areas of the glove. Preferably, the ribs 702 are spaced apart between ¹⁄₁₆" and ¼."

Figure 8:
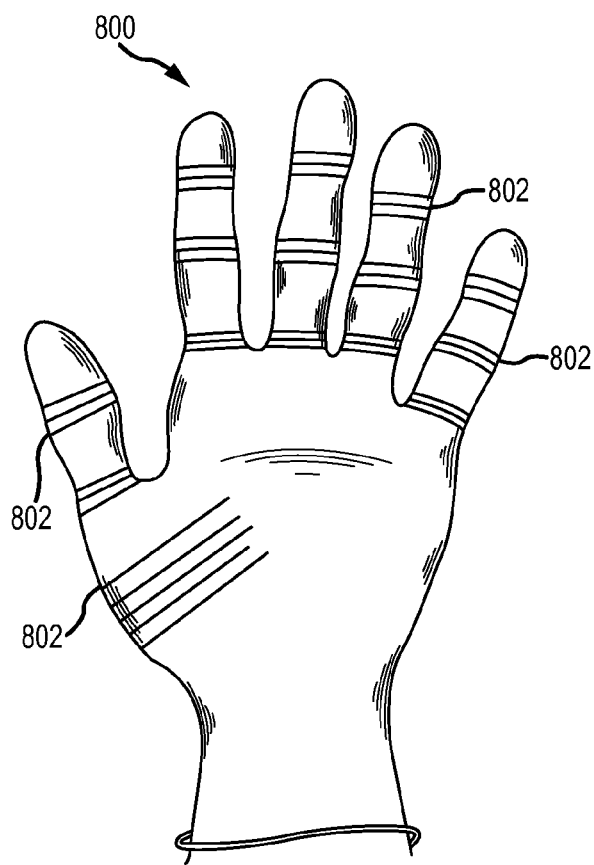
FIG. 8 depicts a top view (wherein the flex angles of the joints cannot be readily seen) of an exemplary glove that includes a pattern of ribs in selected portions of the glove.

FIG. 8 illustrates a glove 800 according to further exemplary embodiments of the invention with ribs 802 to assist with easier flexing. Exemplary ribs 802 can be the same as previously described ribs 702, except ribs 802 only extend along the portions of the glove that correspond to the locations of the joints.

Figure 9:
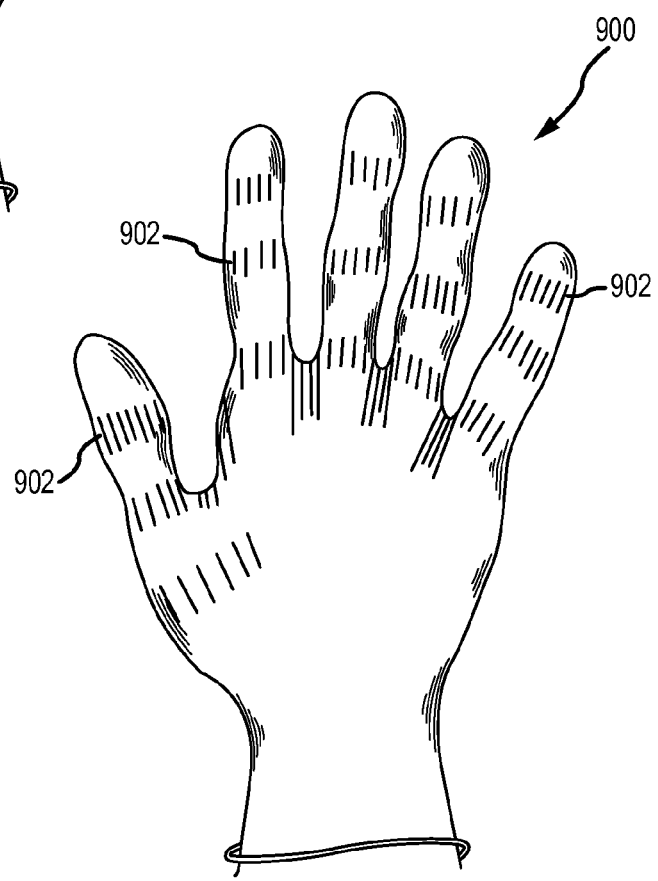
FIG. 9 depicts a top view (wherein the flex angles of the joints cannot be readily seen) of an exemplary glove that includes a pattern of ribs in selected portions of the glove, wherein the ribs are axially oriented to the digits.

FIG. 9 illustrates a glove 900 according to yet further exemplary embodiments of the invention with ribs 902 to assist with easier flexing. Exemplary ribs 902 are formed in the material of glove 900, are axially-aligned along the digits, and are preferably no higher than 2 mm, although any suitable height can be used. The spacing between the ribs may be any suitable spacing and may vary at different areas of the glove. Preferably, the ribs 902 are spaced apart between ¹⁄₁₆" and ¼."

Figure 10:
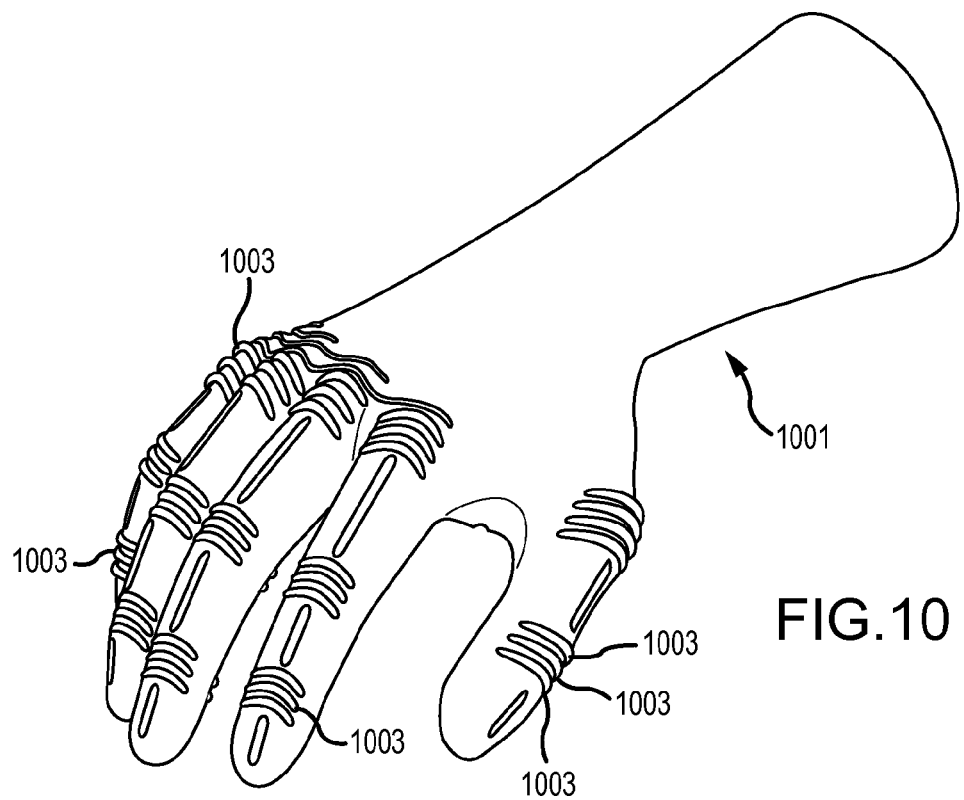
FIG. 10 depicts a top, perspective view of an exemplary glove that includes a pattern of ribs in selected portions of the glove.

FIG. 10 illustrates a glove 1000 according to additional exemplary embodiments of the invention with ribs 1002 to assist with easier flexing. Ribs 1002 are formed in the material of glove 1000 and are preferably no higher than 2 mm, although any suitable height can be used. The ribs are parallel and perpendicular to the long axis of the fingers and the spacing between the ribs 1002 may be any suitable spacing and may vary at different areas of the glove. Preferably, the ribs 1002 are spaced apart between 1/16" and 1/4 and are open at the ends so that they do not connect.

Figure 11:
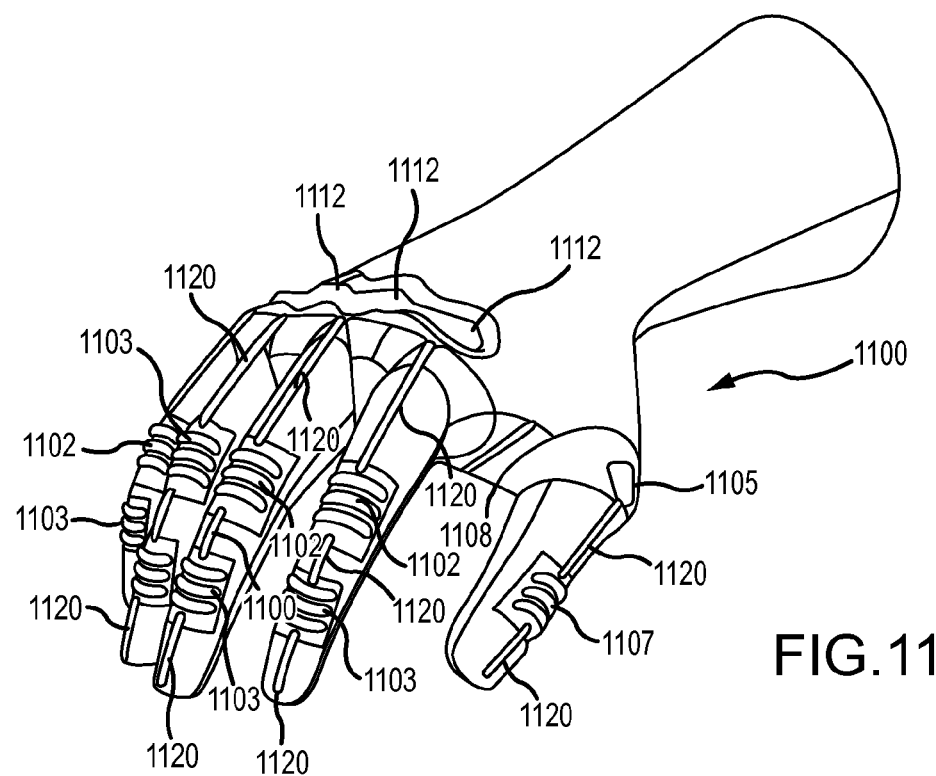
FIG. 11 depicts a top, perspective view of a glove in accordance with an alternate embodiment of the invention.

FIG. 11 illustrates another glove 1100 according to various embodiments of the invention. Glove 1100 includes alternating patterned/textured sections that correspond with the location of each joint separated by non-patterned/non-textured sections that are ribs to provide extra material when the hand or a finger flexes.

These folds of material (ribs) can be located in any suitable place, including between any two joints, between any fingers, between the thumb and index finger, on the dorsum of the hand and/or on the palm of the hand. The folds can provide any suitable amount of material to permit expansion, and in one embodiment provide between 1/16" and 1/4" of extra material. The folds preferably extend outward away from the hand and/or fingers. In the illustrated example, glove 1100 includes a flexible section 1112 corresponding to the MCP of each finger, a flexible section 1102 corresponding to the PIP of each finger, and a flexible section 1103 corresponding to the DIP of each finger. There is a flexible section 1105 corresponding to the MCP of the thumb and a flexible section 1107 corresponding to the IP of the thumb. There is also a longitudinally oriented pattern 1120 between each of the flexible sections and distal from the DIP joints and IP joint that allows for circumferential expansion of the gloves to minimize biasing forces associated with natural digital circumferential expansion that occurs with normal digital flexion.

Figure 15:
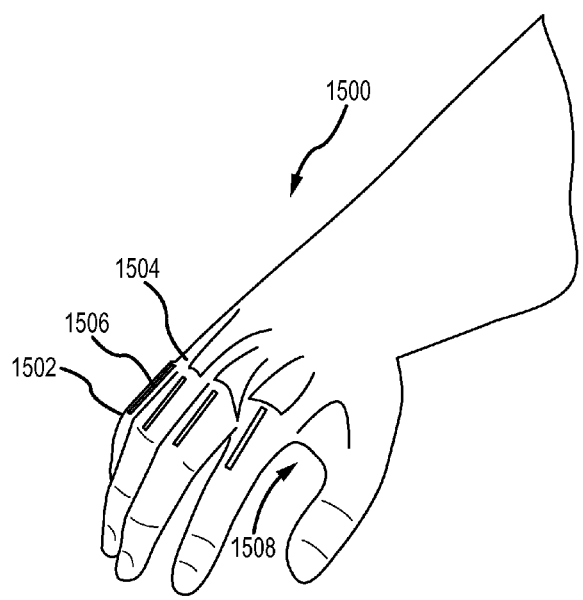
FIG. 15 illustrate another glove having a pattern in accordance with additional embodiments of the invention.
Figure 16B:
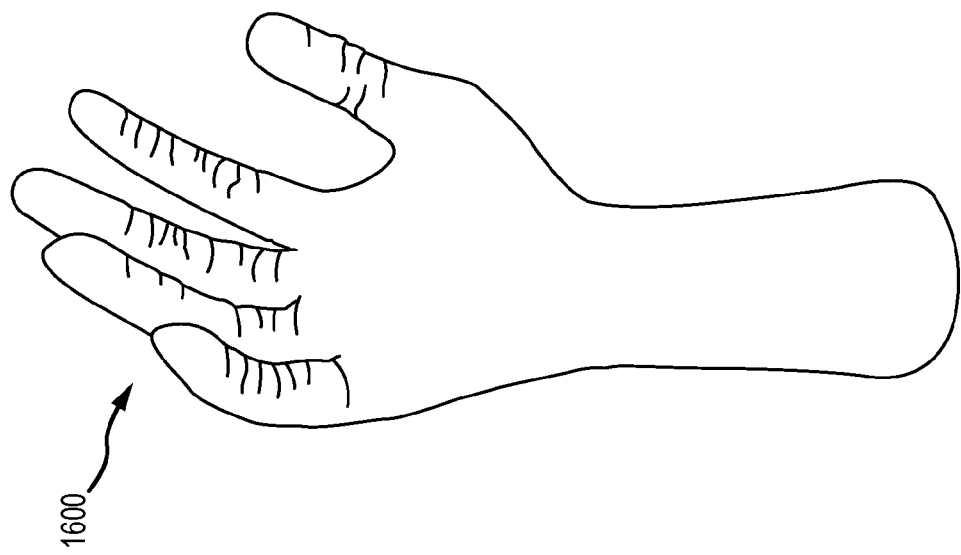
FIGS. 16(*a*) and 16(*b*) illustrate another glove having a pattern in accordance with additional embodiments of the invention.
Figure 16A:
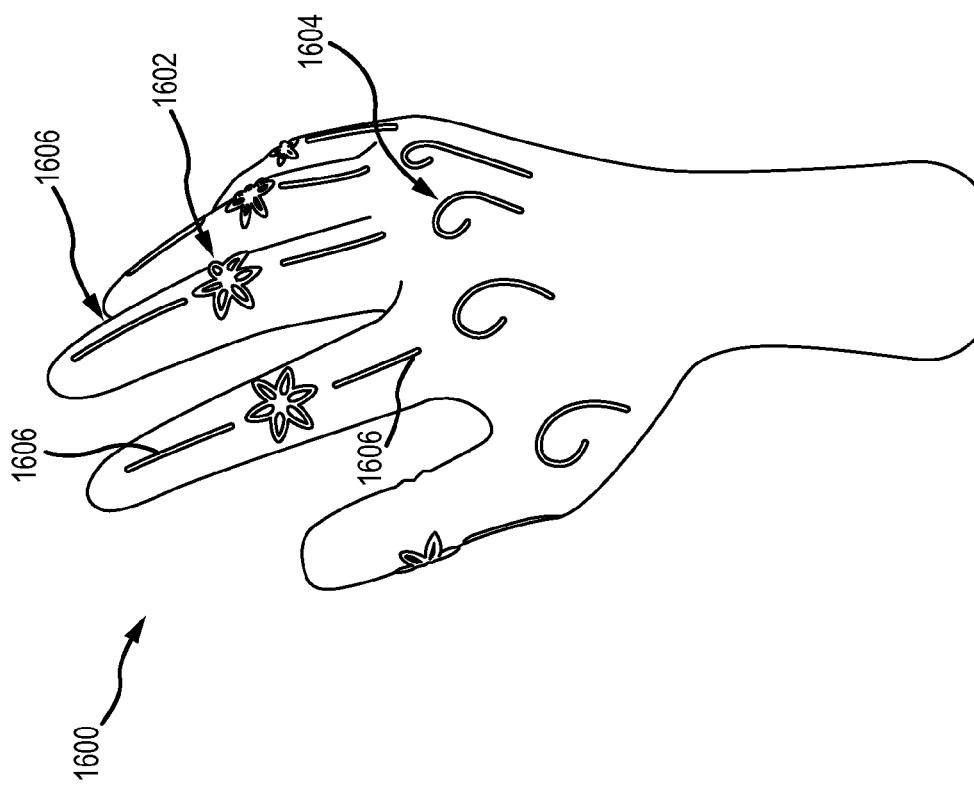

FIGS. 15 and 16(a) and (b) illustrate additional exemplary gloves 1500 and 1600, respectively. Glove 1500 includes PIP joint modifiers 1502, MCP expansion ridges 1504, a proximal expansion groove 1506, and palm expansion channels 1508 in accordance with exemplary embodiments of the invention.

Glove 1600 includes joint strain relief elements 1602, 1604 and longitudinal expansion relief ridges 1606. Strain relief elements 1602, 1604 can be of any suitable shape that provides a desired amount of stain relief—e.g., greater than or equal to 5%, 10%, 25%, 35%, 50%, or the like. As illustrated, elements 1602, 1604 can be decorative, as long as they provide the desired relief of biasing forces. Similarly, ridges 1606 can provide a desired amount of expansion relief, such as greater than or equal to 5%, 10%, 25%, 35%, 50%, or the like.

Figure 22:
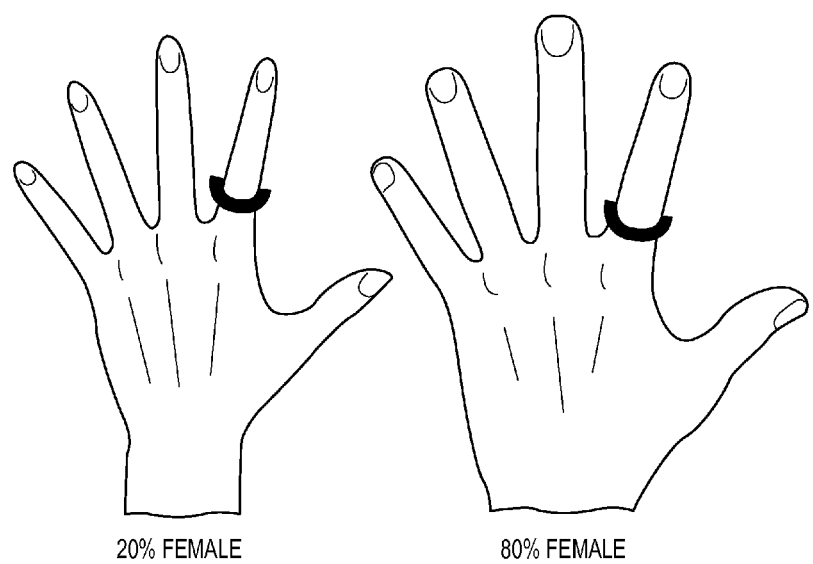
FIG. 22 illustrates a relationship between the circumference of fingers when straight and when flexed.

As previously mentioned, it is also preferred that a glove according to the invention be able to compensate for the expansion of the fingers' respective circumferences when flexed. FIG. 22 illustrates a relationship between the circumferences of fingers when straight and when flexed. A digit circumference can increase from about 15% to about 25% from an extended position to a flex position.

Figure 23:
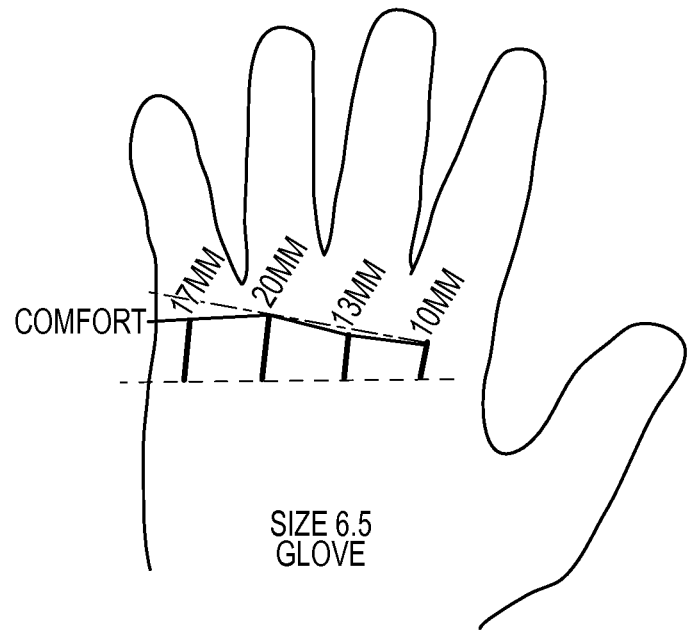
FIG. 23 illustrates an amount of stretch and location of the stretch for a size 6.5 glove at the MCP joints of the fingers.
Figure 24:
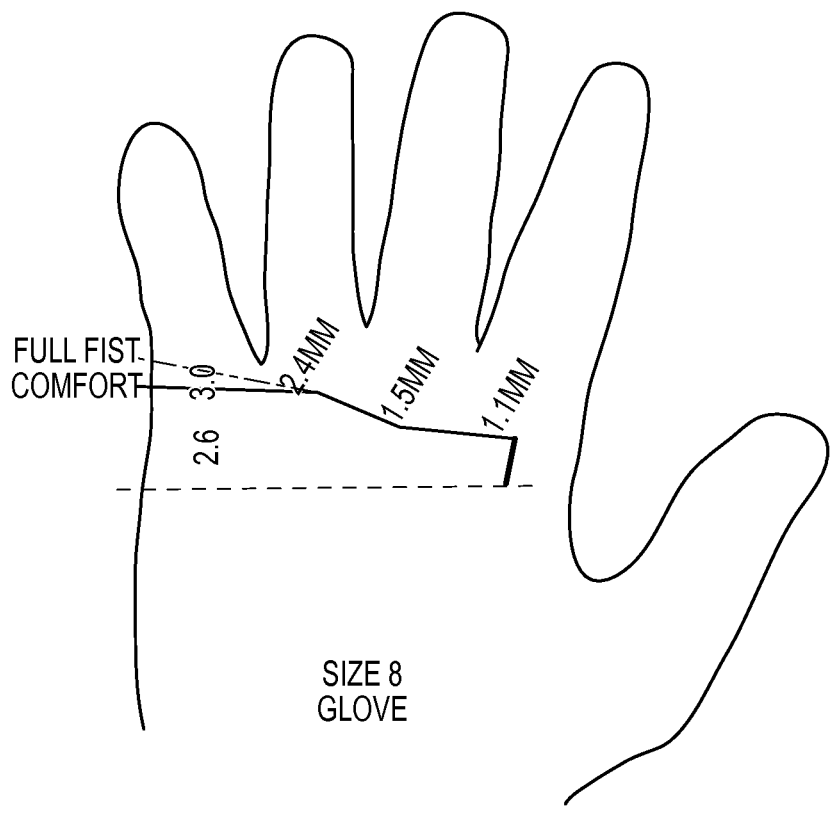
FIG. 24 illustrates an amount of stretch and location of the stretch for a size 8 glove at the MCP joints of the fingers.

FIGS. 23-24 illustrate an amount of stretch and a location for desired stretch in accordance with specific exemplary embodiments of the disclosure. In the illustrated examples, stretch for a size 6.5 glove corresponding to the MCP joints in a hand is illustrated on FIG. 23. Similarly in FIG. 24, an amount of stretch in mm is illustrated for a size 8 glove.

Additionally, gloves according to various exemplary embodiments of the invention can include a two-radius curve, meaning that the angles of the MCP joints are flexed at a greater angle than the other joints.

Materials

A glove according to various aspects of exemplary embodiments of the invention can additionally or alternatively include one or both of the following:

The material forming the glove may have varying thicknesses such that thinner portions are used at positions corresponding to one or more joints on a hand (e.g., where joints or the hand are flexed). For example, a thickness can be reduced by 5%, 10%, 25%, 35%, or 50% in one or more joint areas or a dorsum region, compared to a thickness of the glove material away from the joint and/or dorsum areas.

A glove may be comprised of multiple materials wherein more flexible materials are used at positions corresponding to joints on a hand (e.g., where the joints or the hand are flexed). A more puncture-resistant material may be used at other locations. For example, an elongation at break of the more puncture-resistant material can be about 5%, 10%, 25%, 35%, 50%, 100%, or 200% less than the elongation at break of the more flexible material. The more puncture resistant material can be 5%, 10%, 25%, 35%, 50%, 100%, or 200% more puncture resistant—e.g., as determined according to ASTM F1342.

A glove according to aspects of the invention, in addition to including any or all of the other features referenced in this application, may include portions where the glove material itself is thinner so that less force is required to stretch the thinner portion. Such a glove may also have portions of material thinner than a standard glove would have in order to be more resistant to being punctured.

A glove according to aspects of the invention, in addition to including any or all of the other features referenced in this application, may also be comprised of multiple materials, wherein one material is more flexible and is positioned at locations wherein easier flexing of the gloves is desired.

An aspect of the invention also includes the concept of placing one glove (an outer glove) over another (an inner glove) to create a double glove. A double glove could be packaged as one item in a single package thereby eliminating the packaging of the second glove.

The outer glove may be slightly larger than the inner glove in order to facilitate easier placement of one over the other. For instance a size 8 double might include a size 8 inner glove and a size 8.1 outer glove. Additionally, the inner glove may have a micro-texturing on the outside surface and/or the outer glove may have a micro-texturing on the inner surface to facilitate easier placement of one over the other.

Some specific, non-limiting examples of the invention are as follows:

1. A glove wherein at least one MCP joint is formed at a flex angle of 10-55°.
2. The glove of example 1 wherein at least two MCP joint portions are formed at a flex angle of 10-45°.
3. The glove of example 1 or 2 wherein at least one MCP joint portion is formed at a flex angle of 15-50°.
4. The glove of any of examples 1-3 wherein at least one MCP joint portion is formed at a flex angle of 20-55°.
5. The glove of any of examples 1-4 wherein at least one PIP joint portion is formed at a flex angle of 5-25°.
6. The glove of any of examples 1-5 wherein at least two PIP joint portions are formed at a flex angle of 5-25°.
7. The glove of any of examples 1-6 wherein at least one PIP joint portion is formed at a flex angle of 10-35°.
8. The glove of any of examples 1-7 wherein at least one PIP joint portion is formed at a flex angle of 15-40°.

9. The glove of any of examples 1-8 wherein at least one DIP joint portion is formed at a flex angle of 5-25°.
10. The glove of any of examples 1-9 wherein at least two DIP joint portions are formed at a flex angle of 5-25°.
11. The glove of any of examples 1-10 wherein at least one DIP joint portion is formed at a flex angle of 10-30°.
12. The glove of any of examples 1-11 wherein at least one DIP joint portion is formed at a flex angle of 15-40°.
13. The glove of any of examples 1-12 wherein the thumb MCP joint portion is formed at a flex angle of 10-45°.
14. The glove of any of examples 1-13 wherein the thumb PIP joint portion is formed at a flex angle of 20-50°.
15. A glove wherein at least one PIP joint is formed at a flex angle of 5-40°.
16. The glove of example 15 wherein at least two PIP joint portions are formed at a flex angle of 5-25°.
17. The glove of any of examples 15 or 16 wherein at least one PIP joint portion is formed at a flex angle of 10-35°.
18. The glove of any of examples 15-17 wherein at least one PIP joint portion is formed at a flex angle of 15-40°.
19. The glove of any of examples 15-18 wherein at least one DIP joint portion is formed at a flex angle of 5-25°.
20. The glove of any of examples 15-19 wherein at least two DIP joint portions are formed at a flex angle of 5-25°.
21. The glove of any of examples 15-20 wherein at least one DIP joint portion is formed at a flex angle of 10-30°.
22. The glove of any of examples 15-21 wherein at least one DIP joint portion is formed at a flex angle of 15-40°.
23. The glove of any of examples 15-22 wherein the thumb MCP joint portion is formed at a flex angle of 10-45°.
24. The glove of any of examples 15-23 wherein the thumb PIP joint portion is formed at a flex angle of 20-50°.
25. A glove wherein at least one DIP joint is formed at a flex angle of 5-25°.
26. The glove of example 25 wherein at least two DIP joint portions are formed at a flex angle of 5-25°.
27. The glove of any of examples 25-26 wherein at least one DIP joint portion is formed at a flex angle of 10-30°.
28. The glove of any of examples 25-27 wherein at least one DIP joint portion is formed at a flex angle of 15-40°.
29. The glove of any of examples 25-28 wherein the thumb MCP joint portion is formed at a flex angle of 10-45°.
30. The glove of any of examples 25-29 wherein the thumb PIP joint portion is formed at a flex angle of 20-50°.
31. A glove wherein the MCP joint of the thumb is formed at a flex angle of 10-45°.
32. The glove of example 31 wherein the PIP joint of the thumb is formed at a flex angle of 20°-50°.
33. The glove of any of examples 1-32 wherein there is a pattern between the MCP joint and PIP joint on at least one finger.
34. The glove of example 33 wherein the pattern is on the top of the at least one finger.
35. The glove of any of examples 1-33 wherein the pattern can expand to provide between 1/16" and 1/4" of extra material to allow for expansion of the finger.
36. The glove of any of examples 33-35 wherein the pattern is a longitudinally-extending rib.
37. The glove of any of examples 33-36 wherein there is a pattern between the MCP joint and PIP joint on a plurality of fingers.
38. The glove of example 37 wherein there is a longitudinally-extending rib between the MCP joint and PIP joint on all four fingers.
39. The glove of any of examples 1-38 wherein there is a pattern between the PIP joint and DIP joint on at least one finger.
40. The glove of claim 39 wherein the pattern is on the top of the at least one finger.
41. The glove of any of examples 39-40 wherein the pattern is a longitudinally-extending rib between the PIP joint and DIP joint.
42. The glove of example 41 wherein the rib is on the top of the at least one finger.
43. The glove of any of examples 39-42 wherein the rib can expand to provide between 1/16" and 1/4" of extra material to allow for expansion of the finger.
44. The glove of any of examples 39-43 wherein there is a pattern between the PIP joint and DIP joint on a plurality of fingers.
45. The glove of example 44 wherein there is a pattern between the PIP joint and DIP joint on all four fingers.
46. The glove of examples 44-45 wherein the pattern is a longitudinally-extending rib.
47. The glove of any of examples 1-46 wherein there is a pattern between the MCP joint on the thumb and the DIP joint of the thumb.
48. The glove of example 47 wherein the pattern is on the top of the thumb.
49. The glove of any of examples 47-48 wherein the pattern can expand to provide between 1/16" and 1/4" of extra material to allow for expansion of the thumb.
50. The glove of any of examples 43-49 wherein the pattern is a rib extending along the longitudinal axis between the DIP joint and the IP joint of the thumb.
51. The glove of any of examples 1-50 wherein there is a plurality of patterns, with each pattern located at a different location on the glove.
52. The glove of any of examples 1-51 wherein there is a pattern between the CMC joint and the MCP joint of the thumb.
53. The glove of example 52 wherein the pattern is on the top of the thumb.
54. The glove of any of any of examples 52-53 wherein the pattern can expand to provide between 1/16" and 1/2" of extra material to allow for flexing of the thumb.
55. The glove of any of examples 52-54 wherein the pattern is a rib along the longitudinal axis between the CMC joint and the MCP joint of the thumb.
56. The glove of any of examples 52-55 wherein there is a plurality of patterns.
57. The glove of any of examples 1-56 that includes an outer surface and an inner surface, and a pattern on at least part of one or more of the outer surface and the inner surface, the pattern for reducing biasing forces when the hand or fingers are moved towards the closed position.
58. The glove of example 57 wherein the pattern also reduces biasing forces when the hand or fingers are moved towards the open position.
59. The glove of any of examples 57 or 58 wherein the pattern is entirely on at least part of the outer surface.
60. The glove of any of examples 57 or 58 wherein the pattern is entirely on at least part of the inner surface.
61. The glove of any of examples 33-60 wherein the pattern is selected from one or more of the group consisting of: (a) ribs, (b) raised portions, wherein the center of each raised portion is no greater than either 1/4", 1/8", or 1/16" apart, (c) dimples, or (d) one or more designs.
62. The glove of any of examples 33-61 wherein the pattern is selected from one or more ribs that can provide between 1/16" and 1/4" of extra material to allow for expansion while reducing biasing forces, wherein the one or more ribs can be oriented in any direction.

63. The glove of any of examples 33-61 wherein the pattern is selected from alternating raised portions that can collectively provide for 1/16" to 1/2" of extra material to allow for expansion while reducing biasing forces.
64. The glove of example 63 wherein the raised portions are 10 mm or less in height.
65. The glove of example 63 wherein the raised portions are 5 mm or less in height.
66. The glove of any of examples 63-65 wherein the raised portions have one or more of the following cross-sectional shapes: pyramidal, square, rectangular, semi-oval and semi-circular, and irregular.
67. The glove of any of examples 63-66 wherein each raised portion has a center and the distance between the center of each raised portion is between 1 mm and 10 mm.
68. The glove of any of examples 63-66 wherein each raised portion has a center and the distance between the center of each raised portion is between 2 mm and 5 mm.
69. The glove of example 62 wherein each rib extends 5 mm or less from the outer surface of the glove.
70. The glove of example 62 wherein each rib extends 10 mm or less from the outer surface of the glove.
71. The glove of example 61 wherein the one or more designs are selected from the group consisting of: (a) flowers, (b) letters, (c) concentric circles, (d) numbers, and (e) random designs.
72. The glove of any of examples 1-32 that includes patterns, wherein the patterns provide additional material to permit flexion of the hand while reducing biasing forces, the patterns being at one or more of the following positions on the glove: (a) portions corresponding to one or more of the MCP joints, (b) portions corresponding to one or more of the PIP joints, (c) portions corresponding to one or more of the DIP joints, (d) a portion corresponding to the space between the thumb and index finger, (e) portions corresponding to one or more spaces between any of the fingers, (f) a portion corresponding to at least part of the palm of the hand, and (g) a portion corresponding to at least part of the dorsum of the hand.
73. The glove of any of examples 1-72 wherein the pattern is formed on the dorsum side and/or the palm side of one or more of the following: the MCP joint of the index finger, the MCP joint of the middle finger, the MCP joint of the ring finger, and the MCP joint of the little finger.
74. The glove of any of examples 33-73 wherein the pattern is formed on the dorsum side and/or the palm side of one or more of the following: the PIP joint of the index finger, the PIP joint of the middle finger, the PIP joint of the ring finger, and the PIP joint of the little finger.
75. The glove of any of examples 33-74 wherein the pattern is formed on the dorsum side and/or the palm side of one or more of the following: the DIP joint of the index finger, the DIP joint of the middle finger, the DIP joint of the ring finger, and the DIP joint of the little finger.
76. The glove of any of examples 33-75 wherein the pattern is formed on the dorsum side and/or the palm side of the CMC joint of the thumb.
77. The glove of any of examples 33-76 wherein the pattern is formed on the dorsum side and/or the palm side of the MCP joint of the thumb.
78. The glove of any of examples 33-77 wherein the pattern is formed on the dorsum side and/or the palm side of the PIP joint of the thumb.
79. The glove of any of examples 33-78 wherein the pattern is formed between the thumb and index finger.
80. The glove of any of examples 33-79 wherein the pattern is formed between the index finger and middle finger.
81. The glove of any of examples 33-80 wherein the pattern is formed between the middle finger and ring finger.
82. The glove of any of examples 33-81 wherein the pattern is formed between the ring finger and little finger.
83. The glove of any of examples 33-82 wherein the pattern is formed on at least part of the palm of the hand.
84. The glove of any of examples 33-83 wherein the pattern is formed on at least part of the dorsum of the hand.
85. The glove of any of examples 33-84 wherein the pattern is formed on the palm and extends from approximately the center of the palm to the area between the thumb and index finger.
86. The glove of any of examples 33-85 wherein the pattern is formed on the entire palm of the hand.
87. The glove of any of examples 33-86 wherein the pattern is formed on the dorsum behind the little finger and ring finger.
88. The glove of any of examples 33-87 wherein the pattern is formed on the dorsum behind the little finger, the ring finger and the middle finger.
89. The glove of any of examples 33-88 wherein the pattern is formed on the dorsum behind all of the fingers, and extends at least 1/4" from the MCP joints.
90. The glove of any of examples 33-89 wherein the pattern is formed on the dorsum behind all of the fingers and the thumb, and extends at least 1/4" from the MCP joints on the fingers.
91. The glove of any of examples 87-90 wherein the pattern expands in width the closer it is to the little finger, and has a minimum width of at least 1/4" from the MCP joint on the index finger.
92. The glove of any of examples 1-91 that is formed at a flex angle in the palm region.
93. The glove of any of examples 1-92 wherein the glove is formed at a 5-25° flex angle in the palm region.
94. The glove of any of examples 1-92 wherein the glove is formed at a 10-40° flex angle at the palm.
95. The glove of any of examples 33-91 wherein the pattern covers the index finger on the dorsum and/or palm side from the distal hand to the proximal phalanx.
96. The glove of any of examples 33-95 wherein the pattern covers the dorsum and/or the palm side of the little finger.
97. The glove of any of examples 33-96 wherein the pattern covers the dorsum side of each finger.
98. The glove of any of examples 33-97 wherein the pattern covers the palm side of each finger.
99. The glove of any of examples 33-98 wherein the pattern covers the dorsum side and/or the palm side of the thumb.
100. The glove of any of examples 72-99 wherein the pattern comprises one or more of the group selected from: (a) ribs, (b) raised portions, wherein the center of each raised portion is no greater than either 1/4", 1/8", or 1/16" apart, (c) dimples, or (d) one or more designs.
101. The glove of example 100 wherein the raised portions comprise one or more of the group selected from: the one or more designs are selected from the group consisting of: (a) flowers, (b) letters, (c) concentric circles, (d) numbers, and (e) random designs.
102. The glove of any of examples 33-101 wherein each pattern present on a finger provides between 1/16" and 3/8" of additional material to reduce biasing force during flexion.
103. The glove of any of examples 33-102 wherein each pattern present on the dorsum provides between 1/8" and 1/2" of additional material to reduce biasing force during flexion.

104. The glove of any of examples 33-103 wherein each pattern present on the palm provides between ⅛" and ½" of additional material to reduce biasing force during flexion.
105. The glove of any of examples 33-104 wherein a pattern present between the thumb and index finger provides between ¼" and ½" of additional material to reduce biasing force during flexion.
106. The glove of any of examples 33-105 wherein a pattern present between any two fingers provides between ¹⁄₁₆" and ½" of additional material to reduce biasing force during flexion.
107. A glove with portions formed as follows: (a) a MCP joint of the index finger has a flex angle of 10°-30°, and (b) a PIP joint portion on the same finger is formed at a flex angle greater than the flex angle at which the MCP joint portion is formed.
108. The glove of example 107 wherein the PIP joint portion is formed at a flex angle of between 30° and 45°.
109. The glove of example 107 or 108 that includes a DIP joint portion on the same finger formed at a flex angle of less than the flex angle of the MCP joint.
110. The glove of example 110 wherein the DIP joint portion is formed at a flex angle of 0°-20°.
111. The glove of any of examples 107-110 wherein the flex angle of the MCP joint portion is 25°.
112. The glove of any of examples 107-111 wherein the flex angle of the PIP joint portion is 40°.
113. A glove with portions formed as follows: (a) a MCP joint portion of the middle finger has a flex angle of 10°-30°, and (b) a PIP joint portion on the same finger formed at a flex angle greater than the flex angle at which the MCP joint portion is formed.
114. The glove of example 113 wherein the PIP joint portion is formed at a flex angle of between 30° and 45°.
115. The glove of any of examples 113 or 114 wherein the finger includes a DIP joint formed at a flex angle of less than the flex angle of the MCP joint portion.
116. The glove of example 115 wherein the DIP joint portion is formed at a flex angle of 0°-20°
117. The glove of any of examples 113-116 wherein the flex angle of the MCP joint portion is 25°.
118. The glove of any of examples 113-117 wherein the flex angle of the PIP joint portion is 40°.
119. A glove with portions formed as follows: (a) a MCP joint of the ring finger has a flex angle of 10°-30°, and (b) a PIP joint portion is formed at a flex angle greater than the flex angle at which the MCP joint portion is formed.
120. A glove with portions formed as follows: (a) a MCP joint of the little finger has a flex angle of 10°-30°, and (b) a PIP joint is formed at a flex angle greater than the flex angle at which the MCP joint portion is formed.
121. The glove of example 119 or 120 wherein the PIP joint portion is formed at a flex angle of between 30° and 45°.
122. The glove of example 119 or 120 wherein the DIP joint portion is formed at a flex angle of less than the flex angle of the MCP joint portion.
123. The glove of any of examples 119 or 120 that includes a DIP joint portion formed at a flex angle of 0°-20°.
124. The glove of any of examples 119-123 wherein the flex angle of the MCP joint portion is 25°.
125. The glove of any of examples 119-124 wherein the flex angle of the PIP joint portion is 40°.
126. The glove of any of examples 119-124 that further includes patterns to assist to alleviating the biasing forces associated with one or more of: (a) closing the hand, (b) opening the hand, (c) flexing or bending the fingers, or (d) moving the thumb.
127. A glove having an index finger portion, a middle finger portion, a ring finger portion, a little finger portion and a thumb portion wherein:
    (a) the section of the index finger portion corresponding to the index finger PIP joint is at an angle; and
    (b) the section of the middle finger portion corresponding to the middle finger PIP joint is formed at an angle equal to or greater than the angle of the section of the index finger portion corresponding to the index finger PIP joint.
128. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
129. The glove of example 128 that further includes one of the structures as set forth in examples 1-127 or 130-144.
130. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
131. The glove of example 130 that further includes one of the structures as set forth in examples 1-127 or 133-144.
132. The glove of either of examples 130 or 131 wherein the thinner portion(s) are between 10° and 50° thinner than the thicker portions.
133. A glove wherein one or more of the following portions is formed as follows: (a) the portion corresponding to the DIP joint of the index finger is formed at a 5-25° flex angle, (b) the portion corresponding to the DIP joint of the middle finger is at a 5-25° flex angle, (c) the portion corresponding to the DIP joint of the ring finger is formed at a 10-30° flex angle, and (d) the portion corresponding to the DIP joint of the little finger is formed at a 15-40° flex angle.
134. The glove of example 133 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.
135. The glove of any of examples 133-134 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.
136. The glove of any of examples 133-135 wherein the portion corresponding to the CMC joint of the thumb is formed at a flex angle of 5-25°.
137. The glove of any of examples 133-136 wherein the thumb CMC joint is positioned such that the entire thumb axis is positioned in its relaxed plane.
138. The glove of example 137 wherein the thumb is abducted out of the plane of the palm in a partially opposed position to the plane of the palm.

139. The glove of any of examples 133-138 wherein the flex angle of the DIP joint is less than the flex angle of the corresponding MCP joint.
140. The glove of example 36 wherein the rib is on the top surface of the finger.
141. The glove of example 38 wherein each rib is on the top surface of the finger.
142. The glove of example 46 wherein each rib can provide between 1/16" and 1/4" of extra material.
143. A glove formed at the natural cascading position shown in FIG. 21 plus or minus 10° for each flex angle.
144. The glove of any of examples 133-143 that further includes one or more patterns.

Having thus described preferred embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A medical glove, comprising:
a molded latex or latex-free elastomeric material, and the glove including:
a body portion, a set of finger portions, and a thumb portion; and the finger portions including an index finger portion, a middle finger portion, a ring finger portion and a little finger portion;
the body portion having a proximal opening and a distal area including respective finger openings for each of the finger portions where the finger portions are joined at the finger openings to the body portion, and the finger portions each extend along a long axis away from the finger opening, and the body portion includes a palm region, and a dorsum region which has a lateral side and a medial side and is connected on the lateral side and on the medial side to the palm region, and includes a thumb opening into the thumb portion where the thumb portion is joined at the thumb opening to the body portion and the thumb portion extends along a long axis away from the thumb opening;
the finger portions each sequentially include a MCP joint portion, a proximal phalange portion, a PIP joint portion, a middle phalange portion, a DIP joint portion, and a distal phalange portion; and the thumb member sequentially includes a MCP joint portion, a proximal phalange portion, an IP joint portion, and a distal phalange portion;
wherein for each finger portion, the MCP joint portion, the PIP joint portion and the DIP joint portion are each formed at an angle along the long axis of the finger portion so as to collectively curve the finger portion toward the palm region, and for the thumb portion, the MCP joint portion and the IP joint portion are each formed at an angle along the long axis of the thumb portion so as to collectively curve the thumb portion toward the palm region;
wherein for each finger portion, the angle of the MCP joint portion is greater than the angle for the respective PIP joint portion and for the respective DIP joint portions for each finger portion;
wherein the angle of the index finger MCP joint portion is greater than the angle of the little finger MCP joint portion;
wherein the dorsum region includes a pattern comprising at least one projection of material proximal to the finger opening for each finger portion and there are more projections of material proximal to the opening of the little finger opening than there are proximal to the opening of the index finger opening;
wherein each of the finger portions and the thumb portion includes at least one projection of material which extends in the direction of the long axis so as to accommodate an expansion in diameter in a fully flexed position of a finger portion and the thumb portion; and
wherein for each finger portion, the MCP joint portion, the PIP joint portion and the DIP joint portion each include at least one projection of material which extends across the long axis of the finger portion, and for the thumb portion, the MCP joint portion and the IP joint portion each include at least one projection of material which extends across the long axis of the thumb portion.

* * * * *